US008084204B2

(12) United States Patent
Stojanovic et al.

(10) Patent No.: US 8,084,204 B2
(45) Date of Patent: Dec. 27, 2011

(54) DISPLACEMENT ASSAY FOR DETECTION OF SMALL MOLECULES

(75) Inventors: Milan N. Stojanovic, Fort Lee, NJ (US); Donald W. Landry, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 576 days.

(21) Appl. No.: 12/148,999

(22) Filed: Apr. 24, 2008

(65) Prior Publication Data

US 2008/0286877 A1 Nov. 20, 2008

Related U.S. Application Data

(62) Division of application No. 11/123,648, filed on May 6, 2005, now Pat. No. 7,381,531, which is a division of application No. 10/126,727, filed on Apr. 19, 2002, now abandoned.

(51) Int. Cl.
 *C12Q 1/68* (2006.01)
(52) U.S. Cl. ............................................. 435/6.1
(58) Field of Classification Search .................. None
 See application file for complete search history.

(56) References Cited

U.S. PATENT DOCUMENTS

| | | | |
|---|---|---|---|
| 5,270,163 A | 12/1993 | Gold et al. | |
| 5,580,733 A * | 12/1996 | Levis et al. | 435/6 |
| 5,597,696 A | 1/1997 | Linn et al. | |
| 5,627,030 A | 5/1997 | Pandian et al. | |
| 6,451,535 B1 | 9/2002 | Jenne et al. | |
| 6,472,153 B1 | 10/2002 | Dempcy et al. | |
| 7,115,369 B2 | 10/2006 | Nilesen-Hamilton | |
| 7,122,178 B1 | 10/2006 | Simmons et al. | |
| 7,381,531 B2 | 6/2008 | Stojanovic et al. | |
| 7,470,516 B2 | 12/2008 | Stojanovic et al. | |
| 2003/0198966 A1 | 10/2003 | Stojanovic et al. | |
| 2004/0070426 A1 | 4/2004 | Stojanovic et al. | |
| 2005/0130208 A1 | 6/2005 | Stojanovic et al. | |
| 2006/0172320 A1 | 8/2006 | Stojanovic et al. | |

OTHER PUBLICATIONS

Wu et al., Nucleic Acids Research, vol. 27, No. 6, pp. 1512-1516, 1999.*
Stojanovic et al., J. Am. Chem. Soc., vol. 123, pp. 4928-4931, 2001.*
Axel, R. "Molecular logic of smell" Sci. Am. 1995, 273, 154.
Alberth, K. J.; Lewis, N. S.; Schauer, C. L.; Sotzing, G. A.; Stitzel, S. E.I, Vaid, T. P.; Walt D. R Chem. Rev. 2000, 100, 2595.
Schauer, C. L., Steemers, F. J.; Walt, D. R. J. Am. Chem. Soc. 2001, 123, 9443.
Lavigne, J. J.; Anslyn, E. V. Angew. Chem. Int. Ed. 2001, 40(17), 3118.
Stojanovic, M. N.; Landry, D. W. J. Am. Chem. Soc. 2002, 124, 9678.
Lu, M.; Guo, Q.; Mueller, J. E.; Kemper, B.; Studier, F. W.; Seeman, N. C.; Kallenbach, N. R. J.Biol. Chem. 1990, 265, 16778.
"Molecular Recognition" Gellman, S. (Guest Edt.) Chem.Rev. 1997, 97, special thematic issue.
Ariga, K.; Terasaka, Y.; Sakai, D.; Tsuji, H.; Kikuchi, J. J. Am. Chem. Soc. 2000, 122, 7835-7836.
Castellano, R. K.; Craig, S. L.; Nuckolls, C.; Rebek, J. Jr. J. Am. Chem. Soc. 2000, 122, 7876-7882.
Breslow, R., Dong, D. S.; Chem. Rev. 1998, 98, 1997-2011.
De Silva, A. P.; Gunaratne, H. Q. N.; Gunnlaugsson, T.; Huxley, A. J. M.; McCoy, C. P.; Rademacher J. T.; Rice, T. E. Chem. Rev. 1997, 97 (15), 1515-1566.
Ikeda H.; Nakamura, M.; Nobuyuki, I.; Oguma, N.; Nakamura, A.; Ikeda, T.; Toda, F.; Ueno, A. J. Am. Chem. Soc. 1996, 118, 10980-10988.
Jhaveri, S. D. et al. J. Am. Chem. Soc. 2000, 122, 2469.
Fidanza, J. A.; Ozaki, H.; McLaughlin, L. W. J. Am. Chem. Soc. 1992, 114, 5509.
Jhaveri, S.; Rajendran, M.; Ellington, A. D. Nat. Biotechnol. 2000, 18(12) 1293-1297.
Knemeyer, J.-P.; Marne, N.; Sauer, M. Anal. Chem. 2000, 72, 3717-3724.
Elin, R. J. "Reference Intervals and Laboratory Values" in Cecil Textbook of Medicine (Eds. Bennett, J. C. and Plum, F.) 1996, 20th Ed.
Henning et al., "In vitro selection of RNA molecules that displace cocaine from the membrane . . . " Proc. Nat'l Acad. Sci. USA vol. 95 pp. 14051-14056, Nov. 1998 Biochemistry.
Stojanovic, Milan N.; Prada Paloma de & Landry, Donald W. Aptamer-Based Folding Fluorescent Sensor for Cocaine. J. Am Chem. Soc 2001, 4928-4931.
Stojanovic, Milan N.; Prada Paloma de & Landry, Donald W. J. Fluorescent Sensors Based on Aptamer; Am. Chem. Soc. 2000, 122, 11547-11548.
Broady, E.N.; Gold, L. Rev. Mol. Biotechnol. 2000, 74, 5.
Patel, D., J.; Suri, A.K. Rev. Mol Biotechnal. 2000, 74, 39.
Perry, M.J. in Monoclonal Antibodies: Principles and Application, Birch, J. R.; Lennox, E.S.; Willey-Liss: New York, 1995, pp. 107-120.
Wiskur, S., L.; Ait-Haddou, H.; Lavigne, J. J.; Anslyn, E.V. Acc. Chem. Res. 2001, 34, 963-972.
Beer, P. D.; Gale, P. A. Angew. Chem. Int. Ed. 2001, 40, 486.
Miyaji, H.; Sessler, J.L. Angew. Chem. Int. Ed. 2001, 40, 154.

(Continued)

*Primary Examiner* — Kenneth Horlick
*Assistant Examiner* — Cynthia Wilder
(74) *Attorney, Agent, or Firm* — John P. White; Cooper & Dunham LLP

(57) ABSTRACT

Complex of an anti-cocaine aptamer and the dye diethylthiotricarbocyanine behaves as a calorimetric sensor with attenuation in absorbance at 760 nm for cocaine in the concentration range of 2-5000 µM. Mechanistic studies indicate an intermolecular displacement of the dye as the mechanism of action of the sensor. As the dye is insoluble in buffer, cocaine binding can be detected as displaced dye precipitates and supernatant decolorizes.

29 Claims, 2 Drawing Sheets

OTHER PUBLICATIONS

Rakow, N.A.; Suslick, K.S. Nature 2000, 406, 710.

Chin, J.; Lee, K.J.; Park, S.; Kim, D. H. Nature 1999, 401, 254.

Aoyagi, T.; Nakamura, A.; Ikeda, H.; Mihara, H.; Ueno, A. Anal. Chem. 1997, 69, 659-663.

James, T.D.; Sandavayake, K. R. A. S.; Shinkai, S. Nature 1995, 374, 345.

Cogan, Derek A. and Ellman, Jonathan A.; J. Am. Chem. Soc. 1999, 121, 268.

Tuite, E. Kelly, J. M. Biopolymers 1995, 35, 419.

Wemmer, D. Biopolymers 2001, 52, 197. Cao, Y. W.; Jin, R.; Mirkin, C. A.J. Am. Chem. Soc. 2001, 123, 7961.

Yang, Q.; Goldstein, I.J.; Mei, H.-Y.; Engelke, D. R. Proc. Natl. Acad. Sci. U.S.A. 1998, 95, 5462.

Stojanovic, M., N.; de Prada, P.; Landry, D.W.; J. Am. Chem. Soc. 2001, 123, 4928.

Jhaveri, S.; Rajendran, M.; Ellington, A. D. Nat. Biotechol. 2000, 18, 1293.

Kato, T.; Takemura, T.; T.; Yano, K.; Ikebukuro, K.; Darube, I. Biochim. Biophys. Acta 2000, 1493 (1-2), 12.

Bedner, E.; Du, L.; Traganos, F.; Darzynkiewicz, Z. Cytometry 2001, 43, 38.

Cholic acid competes for binding with Cibacron Blue in allosteric aptamer: Wu, L.; Curran, J.F. Nucleic Acid Res. 1999, 27, 1512.

Osborne, Scott E.; Ellington, Andrew D.; Nucleic Acid Selection and the Challenge of Combinatorial Chemistry; Chem. Rev. 1997, 97 349-370.

International Search Report issued Feb. 10, 2004 in connection with PCT/03/12095.

Pal et al., (1995) "Spectroscopic Probe of the Competitive Binding of Ethidium Bromide and Neomycin to DNA." Spectrochimica Acta 51A(3) : 489-498.

Bedner et al. (2001) "Caffeine Dissociates Complexes Between DNA and Intercalating Dyes: Application for Bleaching Fluorochrome-Stained Cells for Their Subsequent Restaining and Analysis by Laser Scanning Cytometry." Cytometry 43:38-45.

Office Action issued Apr. 12, 2007 in connection with U.S. Appl. No. 11/123,648.

Office Action issued Aug. 3, 2007 in connection with U.S. Appl. No. 11/123,648.

Office Action issued Oct. 1, 2007 in connection with U.S. Appl. No. 11/123,648.

Office Action issued Jan. 8, 2004 in connection with U.S. Appl. No. 10/126,727.

Office Action issued Mar. 26, 2004 in connection with U.S. Appl. No. 10/126,727.

Office Action issued Jul. 22, 2004 in connection with U.S. Appl. No. 10/126,727.

Final Office Action issued Nov. 9, 2004 in connection with U.S. Appl. No. 10/126,727.

Advisory Action Before the Filing of an Appeal Brief issued Mar. 30, 2005 in connection with U.S. Appl. No. 10/126,727.

Office Action issued Jan. 8, 2007 in connection with U.S. Appl. No. 10/990,187.

Office Action issued May 23, 2007 in connection with U.S. Appl. No. 10/990,187.

Final Office Action issued Oct. 1, 2007 in connection with U.S. Appl. No. 10/990,187.

Advisory Action Before the Filing of an Appeal Brief issued Mar. 14, 2008 in connection with U.S. Appl. No. 10/990,187.

Office Action issued Jul. 21, 2008 in connection with U.S. Appl. No. 10/990,187.

Office Action issued Mar. 18, 2009 in connection with U.S. Appl. No. 10/990,187.

* cited by examiner

DISPLACEMENT ASSAY FOR DETECTION OF SMALL MOLECULES

CROSS REFERENCE TO RELATED APPLICATIONS

This application is a divisional of U.S. Ser. No. 11/123,648 filed May 6, 2005, now U.S. Pat. No. 7,381,531 which is a divisional of U.S. Ser. No. 10/126,727, filed Apr. 19, 2002, now abandoned the contents of both of which are hereby incorporated by reference in their entirety into this application.

REFERENCE TO GOVERNMENT RIGHTS

Some of the work reported herein was support by the Counterdrug Technology Center of the Office of National Drug Control Policy and an National Institutes of Health postododtoral fellowship. The United States may have certain rights herein.

BACKGROUND OF THE INVENTION

The present invention relates to a displacement assay for detection of small molecules through detectable spectral changes.

Throughout this application, various publications are referenced to as footnotes or within parentheses. Disclosures of these publications in their entireties are hereby incorporated by reference into this application to more fully describe the state of the art to which this invention pertains. Full bibliographic citations for these references may be found at the end of this application, preceding the claims.

In vitro selection and amplification procedures allow isolation of nucleic-acid receptors or aptamers for almost any small molecule or protein target.[1] Similarly, the immunization can elicit antibodies against most molecular targets.[2] However, no general method exists to engineer such nucleic acid or protein-based receptors to permit direct transduction of the recognition event into a change in the visible spectrum.[3,4a,5]

SUMMARY OF THE INVENTION

If a macromolecule would bind both a chromophore or a fluorophore and the analyte of interest, then the binding of analyte might alter the microenvironment of the chromophore and produce a visible detectable signal of that event, which may be a visible signal. Oligonucleotide receptors are of particular interest, because the interactions between oligonucleotides and dyes have been well studied.[4]

According to the invention, an oligonucleotide receptor for a small molecule or a protein analyte is developed by standard methods. The receptor is complexed with nucleic—acid binding dye. The dye is displaced by an analyte. The useful dynamic range depends upon the binding constant of the original receptor.

The present invention provides a way to detect small molecules and proteins through detectable spectra changes, such as a visible color change, in solution. The present invention provides a direct, single step change, which may be visible, upon analyte detection, similarly advantageous to classic qualitative inorganic and organic analysis.

As used herein, the term "dye" means any compound which has spectral properties, such as a chromophore or fluorophore, which may be in the visible spectrum, but which may also be in any spectrum which is detectable, such as the ultraviolet or infrared spectrum.

According to the invention, a sensor for detecting the presence of a compound is provided, which comprises an oligonucleotide receptor capable of binding to the compound, wherein the receptor comprises a dye attached to the receptor which is released when the receptor binds to the compound.

According to the invention, a method of detecting the presence of a compound in solution is provided which comprises: (a) providing an oligonucleotide receptor with an attached dye, (b) contacting the oligonucleotide receptor with the compound, (c) releasing the dye from the oligonucleotide receptor, and (d) detecting the presence of the released dye, wherein the presence of the released dye indicates the presence of the compound in the solution.

According to the invention, a method of determining the concentration of a compound in solution is provided which comprises: (a) providing an oligonucleotide receptor with an attached dye, (b) contacting the oligonucleotide receptor with the compound, (c) releasing the dye from the oligonucleotide receptor, and (d) measuring a change in absorbance of the dye, wherein the change in absorbance indicates the concentration of the compound in solution.

DETAILED DESCRIPTION OF THE PREFERRED EMBODIMENT

Figure 1:
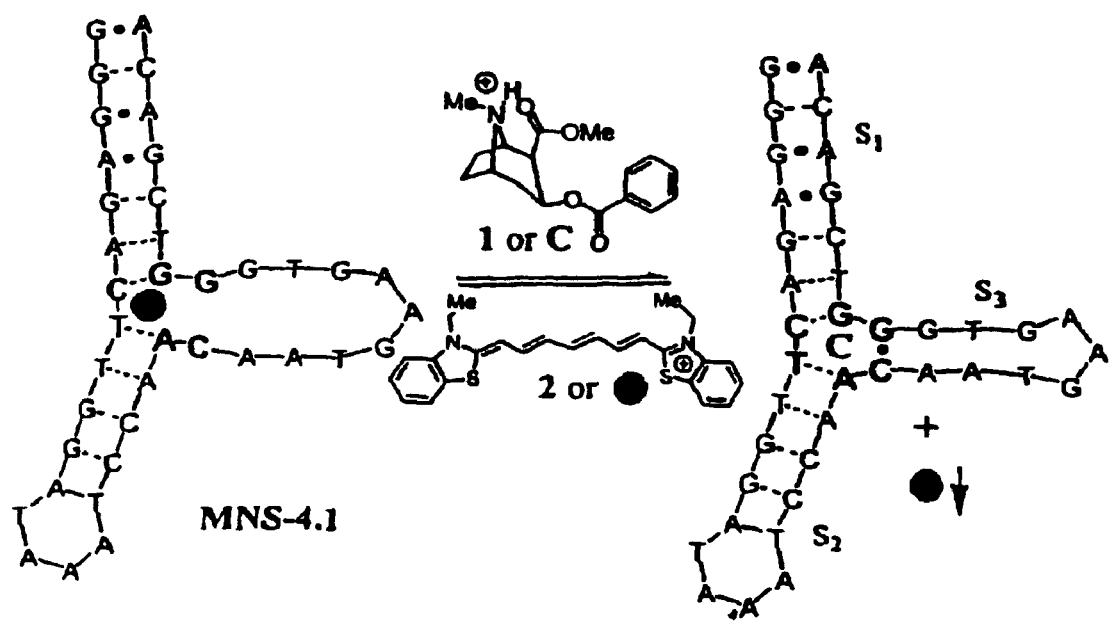
FIG. 1: The aptamer MNS-4.1 complexed with a monomeric dye (dark dot at left); upon interactions with cocaine (C or 1), dye gets displaced, leading to the attenuation of absorbance (lighter dot in middle) and eventual precipitation.

According to the invention, a sensor for detecting the presence of a compound is provided, which comprises an oligonucleotide receptor capable of binding to the compound, wherein the receptor comprises a dye attached to the receptor which is released when the receptor binds to the compound.

The compound may be a small molecule, a polypeptide, or a protein, and could be cocaine.

The receptor may comprise DNA or RNA. The receptor may comprise a hydrophobic pocket which binds the compound, and the hydrophobic pocket may comprise a noncanonical three-way junction. The receptor may comprise a plurality of stems, wherein one or more stems comprises complementary nucleotide base pairing. The structure of one or more stems may exclude complementary nucleotide base pairing.

The attachment of the dye to the receptor may comprise a covalent bond or a non-covalent bond. A plurality of dye molecules may be attached to the receptor. The dye may be a cyanine dye. The dye may be diethylthiotricarbocyanine iodide.

The absorbance of the dye may be attenuated when the dye is released, or enhanced when the dye is released. The wavelength of absorbance of the dye may be modified when the dye is released.

The released dye may be insoluble in solution. The released dye may be detected with a visual indicator. The released dye may precipitate and the supernatant may decolorize. The dye may have a fluorescence property which is changed when the dye is released.

According to the invention, a method of detecting the presence of a compound in solution is provided which comprises: (a) providing an oligonucleotide receptor with an attached dye, (b) contacting the oligonucleotide receptor with the compound, (c) releasing the dye from the oligonucleotide receptor, and (d) detecting the presence of the released dye, wherein the presence of the released dye indicates the presence of the compound in the solution.

The compound may be a small molecule. The compound may be polypeptide. The compound may be a protein. The compound may be cocaine.

The receptor may comprise DNA or RNA. The receptor may comprise a hydrophobic pocket which binds the compound, and the hydrophobic pocket may comprise a noncanonical three-way junction. The receptor may comprise a plurality of stems, wherein one or more stems comprises complementary nucleotide base pairing. The structure of one or more stems may exclude complementary nucleotide base pairing.

The attachment of the dye to the receptor may comprise a covalent bond or a non-covalent bond. A plurality of dye molecules may be attached to the receptor. The dye may be a cyanine dye. The dye may be diethylthiotricarbocyanine iodide.

The absorbance of the dye may be attenuated when the dye is released, or enhanced when the dye is released. The wavelength of absorbance of the dye may be modified when the dye is released. The released dye may be insoluble in solution. The released dye may be detected with a visual indicator. The released dye may precipitate and the supernatant may decolorize. The dye may have a fluorescence property which changes when the dye is released.

According to the invention, a method of determining the concentration of a compound in solution is provided which comprises: (a) providing an oligonucleotide receptor with an attached dye, (b) contacting the oligonucleotide receptor with the compound, (c) releasing the dye from the oligonucleotide receptor, and (d) measuring a change in absorbance of the dye, wherein the change in absorbance indicates the concentration of the compound in solution.

The compound may be small molecule. The compound may be a polypeptide. The compound may be a protein. The compound may be cocaine.

The receptor may comprise DNA or RNA. The receptor may comprise a hydrophobic pocket which binds the compound, and the hydrophobic pocket may comprise a noncanonical three-way junction. The receptor may comprise a plurality of stems, wherein one or more stems comprises complementary nucleotide base pairing. The structure of one or more stems may exclude complementary nucleotide base pairing.

The attachment of the dye to the receptor may comprise a covalent bond or a non-covalent bond. A plurality of dye molecules may be attached to the receptor. The dye may be a cyanine dye. The dye may be diethylthiotricarbocyanine iodide.

The absorbance of the dye may be attenuated when the dye is released. The absorbance of the dye may be enhanced when the dye is released. The wavelength of absorbance of the dye may be modified when the dye is released. The released dye may be insoluble in solution. The released dye may be detected with a visual indicator. The released dye may precipitate and the supernatant may decolorize. The dye may have a fluorescence property which changes when the dye is released.

An anti-cocaine aptamer MNS-4.1[6] (kd<5 µM, FIG. 1) was sought to be converted into a calorimetric sensor.

Cocaine (C) binds MNS-4.1 into a hydrophobic pocket formed by a noncanonical three-way junction, with one of the stems ($S_3$) structured through currently less well-defined non-Watson-Crick interactions. A collection of 35 dyes were screened for changes in visible spectra upon addition of a stock solution of cocaine to a mixture of a given dye and the aptamer. Final cocaine concentration of 20 µM, 200 µM and 2 mM were tested. Many dyes complexed with our aptamer and were displaced only at the highest concentration of cocaine with mild shifts in absorption maxima. In contrast, the absorbance of cyanine dyes exhibited inverse dependence on cocaine concentration. Furthermore, one cyanine dye, diethylthiotricarbocyanine iodide (2), displayed both a significant attenuation of absorbance and a change in the ratio of two relative maxima that dominated the visible spectrum. The calorimetric sensor can be due to fluorescent changes as well. Indocyanines are fluorescent dyes, and their fluorescent spectra changes as well as they are displaced. Diethylthiotricarbocyanine iodide (2) was used in this embodiment to construct a calorimetric molecular sensor for cocaine.

Upon testing various conditions, the following procedure was used to study the concentration-dependent changes in absorption spectra: the mixture of diethylthiotricarbocyanine (c=7 µM) and our aptamer (c=4 µM) was formed in the binding buffer (50 µL, 20 mM TRIS*HCl, pH=7.4, 140 mM NaCl, 5 mM KCl, 2 mM $MgCl_2$), and after equilibration for five minutes, cocaine (stock solutions 100, 10 and 1 mM) was added in portions via micropipette, followed by immediate acquisition of the absorption spectra. At cocaine concentrations increasing from 2 µM to 500 µM, the absorption at 760 nm decreased progressively whereas absorption 670 nm remained nearly constant. At the higher concentrations of the dye and aptamer, the 670 nm peak actually increased upon addition of cocaine. No change was detected in the visible spectra of the aptamer-dye complex upon addition of cocaine metabolites benzoyl ecgonine (3) and ecgonine methyl ester (4) up to 2 mM final concentration, indicating a highly selective interaction with cocaine. The sensitivity and selectivity of the colorimetric sensor was slightly better than of the corresponding fluorescent sensors, indicating that the non-covalent attachment of the dye is less intrusive than the covalent attachments and modification of secondary structure required to construct our fluorescent sensors for cocaine. The release of the dye could be followed by fluorescence techniques.

Interestingly, 2 is poorly soluble in the binding buffer (A<0.1 after standing for 15 minutes) without added aptamer, and addition of the aptamer significantly increases the absorbance of the solution. Based on literature precedent for indocyanine dyes[4a] the two maxima were assigned to the indocyanine monomer (760 nm) and dimer (670 nm) bound to the aptamer. To confirm this assignment, increasing amounts of the aptamer were added into a solution of dye-aptamer complex and the expected increase in absorbance at 760 nm and a decrease at 670 nm was observed.

In order to characterize the structure of the dye-aptamer complex, the binding of the dye to various domains within the aptamer was assessed: the stacked $S_1$ and $S_2$ stems connected through a five nucleotide bulge (GAAAC) in place of $S_3$, and the isolated $S_1$ stem (with added terminal AAAA tetraloop) and the $S_2$ stem-loop. A strong binding of the dye to the aptamer mutant containing both $S_1$ and $S_2$ stem was observed, with unchanged positions of relative maxima. In contrast, no dye-oligonucleotide interactions with the individual stems was observed. None of the three oligonucleotides showed detectable binding to cocaine.

These results indicate that coaxially stacked $S_1$ and $S_2$ stems are the minimal binding motif for the dimer and monomer of 2. The fully matched three-way junctions binds to this dye, with an increased relative proportion of the bound dimer, and this complex retains the capacity to sense cocaine in solution, albeit with a lesser sensitivity. These experiments are consistent with the proposal that the dye binds as both monomer and dimer in the region of the hydrophobic pocket, and that for this binding two surfaces of the coaxially stacked $S_1$ and $S_2$ stems suffice. Addition of cocaine apparently leads to the rapid formation of a ternary complex with reduced absorbance at 760 nm. The increase in absorption at 670 nm observed at the higher concentrations of the dye and aptamer is consistent with: (a) the rapid release (i.e. displacement by cocaine) of the dye complex; (b) much slower displacement of the dimer of dye from the aptamer; (c) competition of released dye with cocaine for the binding to dye-aptamer monomer.

As a result of these studies, it was proposed that cocaine rapidly displaces dye monomer[8] from the aptamer, and that this displacement facilitates the colorimetric readout. The slower kinetics for the interaction of cocaine with the dimer-aptamer complex allows ratiometric readout.

Figure 2:
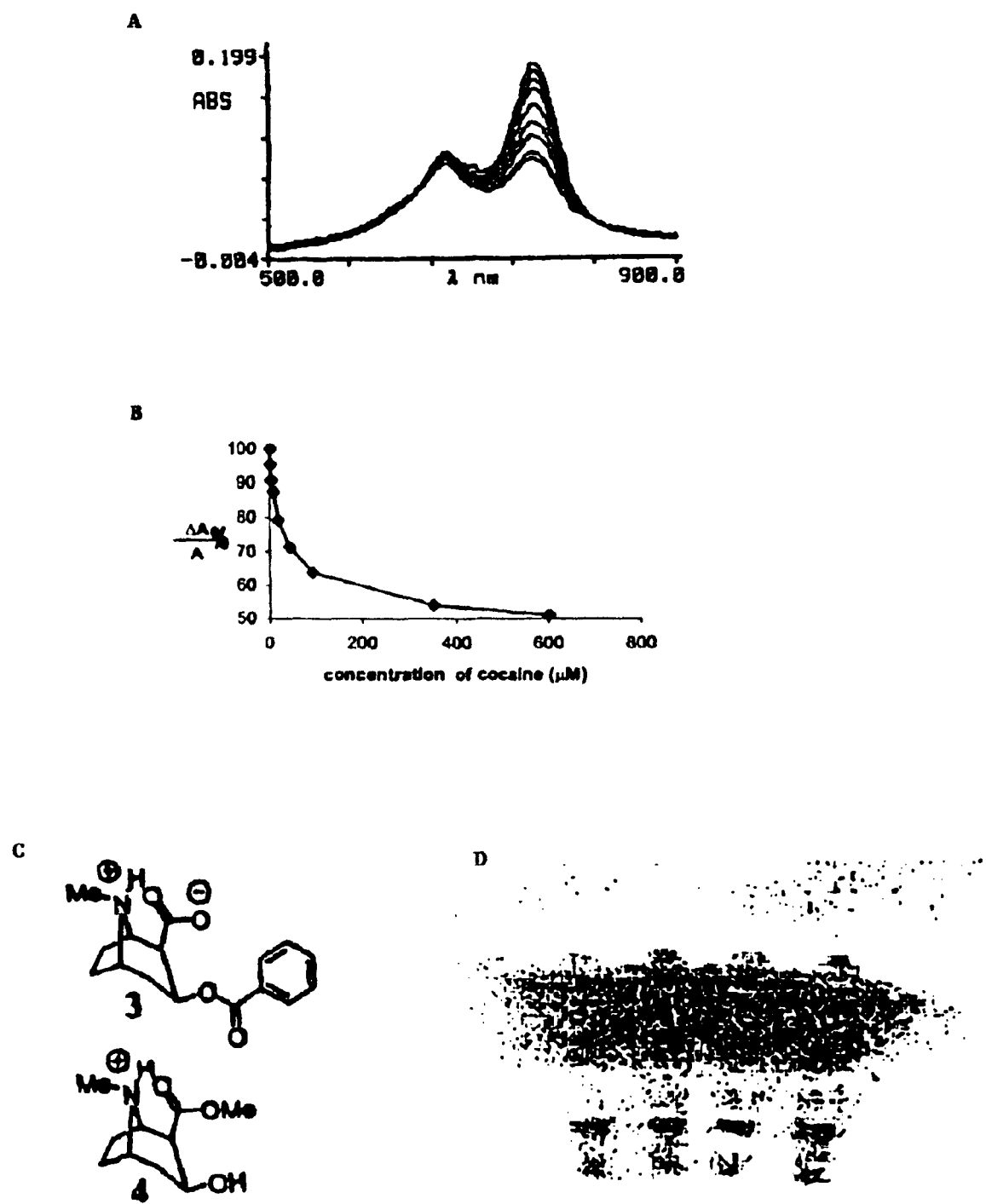
FIG. 2: A. Changes in absorbance upon complexation with cocaine (0.5-600 µM). B. Calibration curve of changes in absorbance vs. Concentration of cocaine; C. Structures of cocaine metabolites benzoyl ecgonine (3) and ecgonine methyl ester (4). D. The dye-aptamer complex in the presence, from left to right, of: benzoyl ecgonine (3), ecgonine methyl ester (4), cocaine (C) and blank control (0).

Finally, a test was done to see whether it was possible to induce a visibly apparent color change through the use of higher dye-aptamer concentrations. Mixing our aptamer with cocaine, cocaine metabolites or blank, followed by the addition of the dye (c(aptamer)=20 and c(dye)=40 µM, c(analytes)=500 µm, (adding dye first, and then analytes gave the same results) resulted in a strongly colored solution ($A_{760}$>1.5, and $A_{670}/A_{760}$~1). Displacement of the dye was readily detected by spectrophotometer, but the faintly darker solution with cocaine could not be easily discerned with the unaided eye. However, after twelve hours one was able to distinguish visually these solutions through the appearance of a blue precipitate and decolorizing of the solution in samples containing cocaine (FIG. 2D). Prolonged incubation (over 48 hours) led to the decolorizing of all solutions, apparently due to hydrolysis of the dye in the cocaine-containing tube remained. These results fully support a mechanism in which cocaine binds to the dye-aptamer complex, destabilizes the complex and induces the release and eventual precipitation of the dye from the solution.

The ability of receptors to undergo visible changes upon recognition of their ligands in "mix and measure" assays could result in simpler and less expensive colormetric analytical procedures, including spot tests for small molecules. The fact that only 35 dyes were screened and more than one dye was able to interact productively with our aptamer underscores the likelihood that for the majority of oligonucleotide receptors the proper dye-aptamer combination could be found through a modest combinatorial approach. For example, the three representative[1b] oligoribonucleotides that bind small molecules, an anti-ATP aptamer, an antitheophiline aptamer and an anti-argininamide HIV TAR, all contain coaxially stacked non-conserved helical stems connected through bulges (similar to the structure of our aptamer without cocaine), which suggests that they would be good candidates for this approach to calorimetric sensing.

Although two dyes have been discussed, any dye could be used that binds to a nucleic acid and which is released when the receptor binds to the compound. The release of the dye may be detectable in the visible spectra, but may also be detectable outside the visible spectra, such as the ultraviolet or infrared spectrum. One may be able to detect lower concentrations of compounds or analytes below the micro molar level, such as in the nano molar level. The present invention is thus not limited to the preferred embodiment and its scope is defined only by way of the following claims.

REFERENCES 1. a) Brody, E. N.; Gold, L. Rev. Mol. Biotechnol. 2000, 74, 5. b) Patel, D., J.; Suri, A. K. ibid. 2000, 74, 39.
2. Perry, M. J. in Monoclonal Antibodies: Principles and Applications Birch, J. R.; Lennox, E. S; Ess.; Willey-Liss: New York, 1995, pp 107-120.
3. a) Wiskur, S., L.; Ait-Haddou, H.; Lavigne, J. J.; Anslyn, E. V. Acc. Chem. Res. 2001, 34, 963-972. b) Bear, P. D.; Gale, P. A. Angew. Chem. Int. Ed. 2001, 40, 486. c) Miyaji, H.; Sessler, J. L. Angew. Chem. Int. Ed. 2001, 40, 154 d) Rakow, N. A.; Suslick, K. S. Nature 2000, 406, 710. E) Chin, J.; Lee, K. J.; Park, S.; Kim, D. H. Nature 1999, 401, 254. f) Aoyagi, T.; Nakamura, A.; Ikeda, H.; Mihara, H.; Ueno, A. Anal. Chem. 1997, 69, 659-663. f) James, T. D.; Sandanayake, K. R. A. S.; Shinkai, S. Nature 1995, 374, 345.
4. a) Smith, J. O.; Olson, D. A.; Armitage, B. A. J. Am. Chem. Soc. 1999, 121, 268 and references therein; b) Tuite, E.; Kelly, J. M. Biopolymers 1995, 35, 419. c) For review on ligands recognizing minor groove of DNA: Wemmer, D. Biopoloymers 2001, 52, 197.
5. For colorimetric determination of peptide nucleic acids-containing duplexes and dyes see ref. 4 a. For calorimetric determinations using gold and gold-coated nanoparticles see: b) Cao, Y. W.; Jin, R.; Mirkin, C. A. J. Am. Chem. Soc. 2001, 123, 7961 and references therein. We have used gold nanoparticles in combination with self-assembling aptameric sensors (ref. 6 a) with some success (MNS, DWL reported at $222^{nd}$ ACS National Meeting, Chicago, 2001). Interactions of saccharides with their DNA ligands can be followed by changes in UV spectra; c) Yang, Q.; Goldstein, I. J.; Mei, H.-Y.; Engelke, D. R. Proc. Natl. Acad. Sci. U.S.A. 1998, 95, 5462.
6. We used this aptamer to construct fluorescent sensors for cocaine: a) Stojanovic, M., N.; de Prada, P.; Landry, D. W.; J. Am. Chem. Soc. 2001, 123, 4928 and references therein. For other approaches to fluorescent aptameric sensors see: b) Jhaveri, S.; Rajendran, M.; Ellington, A. D. Nat. Biotechol. 2000, 18, 1293 and references therein.
7. For binding of small molecules into the canonical three-way junctions see: Kato, T.; Takemura, T.; Yano, K.; Ikebukuro, K.; Darube, I. Biochim. Biophys. Acta 2000, 1493 (1-2), 12, and references therein.
8. Caffeine displaces complexes between DNA and intercalating dyes: a) Bedner, E.; Du, L.; Traganos, F.; Darzynkiewicz, Z. Cytometry 2001, 43, 38. Cholic acid competes for binding with Cibacron Blue in allosteric aptamer: Wu, L.; Curran, J. F. Nucleic Acid Res. 1999, 27, 1512.

We claim:
1. A method of detecting the presence of a small molecule in a solution which comprises:
 (a) providing an oligonucleotide receptor with an attached dye, wherein the attachment of the dye to the receptor comprises a non-covalent bond;
 (b) contacting the oligonucleotide receptor with the small molecule in the solution under conditions permitting the small molecule to bind to the oligonucleotide receptor and release the dye from the oligonucleotide receptor; and

(c) detecting the presence of the released dye, wherein the presence of the released dye indicates the presence of the small molecule in the solution.

2. The method of claim 1, wherein the small molecule is cocaine.

3. The method of claim 1, wherein the receptor comprises DNA.

4. The method of claim 1, wherein the receptor comprises RNA.

5. The method of claim 1, wherein the receptor comprises a hydrophobic pocket which binds the small molecule.

6. The method of claim 5, wherein the hydrophobic pocket comprises a noncanonical three-way junction.

7. The method of claim 1, wherein the receptor comprises a plurality of stems, wherein one or more stems comprises complementary nucleotide base pairing.

8. The method of claim 1, wherein the receptor comprises a plurality of stems, wherein the structure of one or more stems excludes complementary nucleotide base pairing.

9. The method of claim 1, wherein a plurality of dye molecules are attached to the receptor.

10. The method of claim 1, wherein the dye is a cyanine dye.

11. The method of claim 1, wherein the dye is diethylthiotricarbocyanine iodide.

12. The method of claim 1, wherein the absorbance of the dye is attenuated when the dye is released.

13. The method of claim 1, wherein the absorbance of the dye is enhanced when the dye is released.

14. The method of claim 1, wherein the wavelength of absorbance of the dye is modified when the dye is released.

15. The method of claim 1, wherein the released dye is insoluble in solution.

16. The method of claim 1, wherein the released dye is detected with a visual indicator.

17. The method of claim 1, wherein the released dye precipitates and the supernatant decolorizes.

18. The method of claim 1 wherein the dye has a fluorescence property which changes when the dye is released.

19. A method of determining the concentration of a small molecule in a solution which comprises:
(a) contacting an oligonucleotide receptor having a dye attached thereto with the small molecule under conditions permitting the small molecule to bind to the oligonucleotide receptor, wherein the attachment of the dye to the receptor comprises a non-covalent bond and release the dye from the oligonucleotide receptor;
(b) measuring a concentration-dependent change in absorbance of the dye; and
(c) determining from a calibration curve the concentration of the small molecule in the solution indicated by the concentration-dependent change in absorbance.

20. The method of claim 19, wherein the small molecule is cocaine.

21. The method of claim 19, wherein the receptor comprises DNA.

22. The method of claim 19, wherein the receptor comprises RNA.

23. The method of claim 19, wherein the receptor comprises a hydrophobic pocket which binds the small molecule.

24. The method of claim 23, wherein the hydrophobic pocket comprises a noncanonical three-way junction.

25. The method of claim 19, wherein the receptor comprises a plurality of stems, wherein one or more stems comprises complementary nucleotide base pairing.

26. The method of claim 19, wherein the receptor comprises a plurality of stems, wherein the structure of one or more stems excludes complementary nucleotide base pairing.

27. The method of claim 19, wherein a plurality of dye molecules are attached to the receptor.

28. The method of claim 19, wherein the dye is a cyanine dye.

29. The method of claim 19, wherein the dye is diethylthiotricarbocyanine iodide.

\* \* \* \* \*